United States Patent
Fleischmann

(10) Patent No.: US 10,206,755 B2
(45) Date of Patent: Feb. 19, 2019

(54) METHOD FOR STRETCHING THE SKIN

(71) Applicant: Wilhelm Fleischmann, Freiburg i. Br. (DE)

(72) Inventor: Wilhelm Fleischmann, Freiburg i. Br. (DE)

( * ) Notice: Subject to any disclaimer, the term of this patent is extended or adjusted under 35 U.S.C. 154(b) by 46 days.

(21) Appl. No.: 15/210,244

(22) Filed: Jul. 14, 2016

(65) Prior Publication Data

US 2016/0317150 A1 Nov. 3, 2016

Related U.S. Application Data

(63) Continuation of application No. 12/530,186, filed as application No. PCT/EP2008/001574 on Feb. 28, 2008, now Pat. No. 9,414,840.

(30) Foreign Application Priority Data

Mar. 8, 2007 (DE) .................. 10 2007 011 570

(51) Int. Cl.
*A61B 17/08* (2006.01)
*A61B 90/00* (2016.01)
*A61B 17/02* (2006.01)
*A61B 17/00* (2006.01)

(52) U.S. Cl.
CPC .............. *A61B 90/02* (2016.02); *A61B 17/08* (2013.01); *A61B 17/02* (2013.01); *A61B 2017/00407* (2013.01); *A61B 2017/00884* (2013.01); *A61B 2017/081* (2013.01); *A61B 2017/088* (2013.01)

(58) Field of Classification Search
CPC .............. A61B 17/08; A61B 2017/081; A61B 2017/088; A61B 2017/0084; A61B 19/24
See application file for complete search history.

(56) References Cited

U.S. PATENT DOCUMENTS

| 268,632 | A | 12/1882 | Danforth |
| 583,455 | A | 6/1897 | Bush |
| 2,450,194 | A | 9/1948 | Albert |
| 2,669,747 | A | 2/1954 | Detaranto |
| 3,825,010 | A | 7/1974 | McDonald |

(Continued)

FOREIGN PATENT DOCUMENTS

| DE | 4335432 | 4/1995 |
| DE | 19832634 | 1/2000 |

(Continued)

OTHER PUBLICATIONS

Keetenwirk-Praxis, "Neue Musterungsmoglichkeiten," 2: 47-48 (2001).

(Continued)

*Primary Examiner* — Robert Lynch

(74) *Attorney, Agent, or Firm* — Akerman LLP; Peter A. Chiabotti

(57) ABSTRACT

In a device for stretching the skin, particularly for closing a wound, anchoring elements are anchored in the skin. The anchoring elements are movable on a guide device. First anchoring elements are anchored in the skin of the edge of the wound. Second anchoring elements are adjustable on the guide device in the stretching direction behind the first anchoring elements in relation to and independently of said first anchoring elements.

18 Claims, 4 Drawing Sheets

(56) References Cited

U.S. PATENT DOCUMENTS

| | | |
|---|---|---|
| 3,971,384 A | 7/1976 | Hasson |
| 4,073,298 A | 2/1978 | Le Roy |
| 4,382,441 A | 5/1983 | Svedman |
| 4,409,968 A | 10/1983 | Drummond |
| 4,422,451 A | 12/1983 | Kalamchi |
| 4,430,998 A | 2/1984 | Harvey et al. |
| 4,641,636 A | 2/1987 | Cotrel |
| 4,854,304 A | 8/1989 | Zielke |
| 4,896,680 A | 1/1990 | Hirshowitz |
| 5,127,412 A | 7/1992 | Cosmetto et al. |
| 5,176,663 A | 1/1993 | Svedman et al. |
| 5,203,783 A | 4/1993 | Härle |
| 5,234,462 A | 8/1993 | Pavletic |
| 5,263,971 A | 11/1993 | Hirshowitz et al. |
| 5,291,887 A | 3/1994 | Stanley et al. |
| 5,374,267 A | 12/1994 | Siegal |
| 5,441,540 A | 8/1995 | Kim |
| 5,478,340 A | 12/1995 | Kluger |
| 5,486,196 A | 1/1996 | Hirshowitz et al. |
| 5,507,775 A | 4/1996 | Ger et al. |
| 5,531,790 A | 7/1996 | Frechet et al. |
| 5,549,640 A | 8/1996 | Fontenot |
| 5,549,713 A | 8/1996 | Kim |
| 5,571,138 A | 11/1996 | Blomqvist et al. |
| 5,584,856 A | 12/1996 | Jameel et al. |
| 5,589,245 A | 12/1996 | Roell |
| 5,618,310 A | 4/1997 | Ger et al. |
| 5,636,643 A | 7/1997 | Argenta et al. |
| 5,645,081 A | 7/1997 | Argenta et al. |
| 5,653,699 A | 8/1997 | Reed et al. |
| 5,662,714 A | 9/1997 | Charvin et al. |
| 5,723,009 A | 3/1998 | Frechet et al. |
| 5,733,305 A | 3/1998 | Fleischmann |
| 5,759,193 A | 6/1998 | Burbank et al. |
| 5,807,295 A | 9/1998 | Hutcheon et al. |
| 5,814,067 A | 9/1998 | Fleischmann |
| 5,893,879 A | 4/1999 | Hirshowitz |
| 5,928,231 A | 7/1999 | Klein et al. |
| 6,010,524 A | 1/2000 | Fleischmann |
| 6,106,544 A | 8/2000 | Brazeau |
| 6,120,525 A | 9/2000 | Westcott |
| 6,142,982 A | 11/2000 | Hunt et al. |
| 6,254,624 B1 | 7/2001 | Oddsen et al. |
| 6,315,780 B1 | 11/2001 | Lalonde |
| 6,398,767 B1 | 6/2002 | Fleischmann |
| 6,471,715 B1 | 10/2002 | Weiss |
| 6,733,537 B1 | 5/2004 | Fields et al. |
| 6,755,052 B1 | 6/2004 | Sytz |
| 6,755,807 B2 | 6/2004 | Risk et al. |
| 7,208,006 B2 | 4/2007 | Fleischmann |
| 7,235,090 B2 | 6/2007 | Buckman et al. |
| 7,520,872 B2 | 4/2009 | Biggie et al. |
| 8,092,491 B2 | 1/2012 | Fleischmann |
| 8,114,124 B2 | 2/2012 | Fleischmann |
| 8,376,972 B2 | 2/2013 | Fleischmann |
| 8,430,908 B2 | 4/2013 | Fleischmann |
| 9,271,730 B2 | 3/2016 | Fleischmann |
| 2002/0188170 A1 | 12/2002 | Santamore et al. |
| 2003/0092969 A1* | 5/2003 | O'Malley ............ A61B 17/02 600/216 |
| 2003/0163160 A1 | 8/2003 | O'Malley et al. |
| 2003/0176890 A1 | 9/2003 | Buckman et al. |
| 2003/0225436 A1 | 12/2003 | Fleischmann |
| 2004/0267309 A1 | 12/2004 | Garvin |
| 2005/0209574 A1 | 9/2005 | Boehringer et al. |
| 2006/0247649 A1 | 11/2006 | Rezach et al. |
| 2007/0156175 A1 | 7/2007 | Weadock et al. |
| 2007/0191885 A1 | 8/2007 | Fleischmann |
| 2007/0213714 A1 | 9/2007 | Justis |
| 2008/0147115 A1 | 6/2008 | O'Malley et al. |
| 2008/0208251 A1 | 8/2008 | Weadock et al. |
| 2008/0312685 A1 | 12/2008 | O'Malley et al. |
| 2009/0326578 A1 | 12/2009 | Ewers et al. |
| 2010/0030260 A1 | 2/2010 | Fleischmann |
| 2015/0359598 A1 | 12/2015 | Fleischmann |

FOREIGN PATENT DOCUMENTS

| | | |
|---|---|---|
| DE | 19844355 | 4/2000 |
| DE | 102 09 122 | 10/2003 |
| EP | 0617152 | 9/1994 |
| EP | 0880953 | 12/1998 |
| EP | 1340461 | 9/2003 |
| EP | 1131024 | 9/2004 |
| FR | 2756722 | 6/1998 |
| FR | 2758711 | 7/1998 |
| GB | 2292526 | 2/1996 |
| RU | 2 021 765 | 10/1994 |
| RU | 1424809 | 9/1998 |
| SU | 1412751 | 7/1988 |
| SU | 1457906 | 2/1989 |
| WO | 9309727 | 5/1993 |
| WO | 95/16416 | 6/1995 |
| WO | 9526698 | 10/1995 |
| WO | 9608223 | 3/1996 |
| WO | 96/18345 | 6/1996 |
| WO | 0018343 | 4/2000 |
| WO | 01/93771 | 12/2001 |
| WO | 10/092455 | 8/2010 |
| WO | 02087481 | 1/2011 |

OTHER PUBLICATIONS

Wollina et al., "Spacer Fabrics—A Potential Tool in the Prevention of Chronic Wounds," Exog Dermatol, 1: 276-278 (2002).

Hirshowitz et al., "Reconstructions of the tip of the nose and ala by load cycling of the nasal skin and harnessing of extra skin," In: Plast Reconstr Surg, 77:316 (1986).

Melis et al., "Primary skin closure of a large groin defect after inguinal lymphadenectomy for penile cancer . . . ," In: The Jour. of Urology, 159(1): 185-187 (1998).

* cited by examiner

METHOD FOR STRETCHING THE SKIN

CROSS REFERENCE TO RELATED APPLICATION

This application is a continuation of, and claims the benefit of U.S. patent application Ser. No. 12/530,186, filed Sep. 7, 2009, which is a § 371 National Phase of PCT/EP2008/001574, filed Feb. 28, 2008, which claims priority to German Patent Application DE 10 2007 011 570.0, filed Mar. 8, 2007, the entireties of which are incorporated by reference herein.

BACKGROUND OF THE INVENTION

The invention relates to a device and method for stretching the skin.

Skin stretching is used in surgical practice to obtain skin for transplantation and in particular for closing large-area wounds by pulling together the edges of the wound.

DE 44 44 130 A1 discloses moving two anchoring elements on guide rails running in the direction of the desired stretching of the skin by means of a threaded spindle, the anchoring elements being movable in an adjustable fashion. The anchoring elements are formed by flanges bearing hooks that may be inserted into the skin. The hooks of both anchoring elements are inserted into the opposing edges of a wound in such a way that the wound is located in the intermediate area between the anchoring elements. If the anchoring elements are moved opposite one another, then the edges of the wound are pulled together. The tensile force acting on the skin of the edges of the wound leads to an increased proliferation of tissue, which benefits and allows the pulling together of the wound edges.

U.S. Pat. No. 4,896,680 discloses a device in which a flexible band ribbed in a transverse manner serves as a guide device. The one end of the band is fixed in the skin by means of an anchoring element in the form of a safety needle. A second such anchoring element is guided on the band in an adjustable manner and locked in the transverse ribs of the band.

U.S. Pat. No. 5,571,138 discloses the use of a flexible band as a guide device for obtaining skin for transplantation, with two anchoring elements being disposed on the band in an adjustable and clampable manner in order to stretch the skin on both sides of the intermediate area between these anchoring elements and to obtain excess skin for transplantation in the intermediate area.

U.S. Pat. No. 5,531,790 discloses a baldness treatment in which the skin with hair on the sides of the head is stretched and pulled together by a device comprising an elastic band that carries one or more rows of hooks as anchoring elements on both ends. The hooks are inserted into the skin on the head with hair such that said skin is pulled together by the elasticity of the band. By arranging multiple rows of anchoring elements, it is possible for larger skin regions to be captured and stretched. The anchoring elements are not provided in an adjustable fashion.

SUMMARY OF THE INVENTION

The object is to create a device for stretching the skin that allows an improved effectiveness of skin proliferation.

This object is achieved by a device for stretching the skin, having the structures and features described herein.

Advantageous embodiments of the disclosure are listed in the subordinate claims.

In the device, according to the disclosure, a pair of first anchoring elements are anchored in the skin. These first anchoring elements are guided opposite one another in an adjustable fashion, whereby the distance between the first anchoring elements and the intermediate area between these anchoring elements is reduced. The skin is stretched on both sides outside of the first anchoring elements. In the most common applications for wound closure, the edges of the wound are pulled together in order to reduce the wound area located between the anchoring elements and to stretch the skin areas adjacent to the edges of the wound.

The tensile force that may be exerted on the skin by these first anchoring elements is limited. If the tensile force is too great, the anchoring elements may tear out of the skin. Even if the anchoring elements do not tear out, it is possible for such a high pressure to be exerted on the skin tissue located in front of the anchoring elements that the skin becomes ischemic and, if the tensile force is maintained for a longer period, becomes necrotic.

The disclosure counteracts this disadvantage in that at least one second anchoring element is disposed behind at least one of the first anchoring elements in the pull direction. This second anchoring element is also anchored in the skin and, due to its arrangement, is located at a greater distance from the intermediate area between the first anchoring elements, for example, from the edge of the wound. The at least one second anchoring element is also adjustable on the guide element. By virtue of their adjustability, the second anchoring elements are able to exert an adjustable tensile force on the skin that is effective at a greater distance from the edge of the wound. This results in the following significant advantages for skin stretching.

Experimental investigations have shown that the tensile force acting on the skin only has a small range. By virtue of the elasticity of the skin, the tensile force dissipates over a stretch of a few centimeters, such that, in human skin, the tensile force generally has no more effect at a distance of 5 or 6 centimeters from the introduction of the tensile force and does not stimulate any tissue proliferation. Using one or more second anchoring elements, an additional tensile force is exerted on the skin at a correspondingly greater distance from the edge of the wound such that a significantly greater skin area may be used for stretching and tissue proliferation.

By means of the second anchoring elements, the skin is already placed under tensile force before the first anchoring element such that the skin that has been pre-stressed by the second anchoring elements needs only to be loaded with a relatively low tensile force by the last first anchoring element in the pulling direction. Therefore, only a low level of force is acting on the skin at each anchoring point due to the individual anchoring elements and particularly due to the first anchoring elements. This prevents the first anchoring elements from tearing out. The pressure exerted by the first anchoring elements on the skin tissue before these anchoring elements may be reduced under the ischemic threshold without impeding tissue proliferation. Skin stretching may therefore also be conducted over a long period of time without damage to the tissue, which results in a quicker and more effective treatment.

The tensile force introduced into the skin by the anchoring elements may be selected to be large enough that ischemia results on the pressure side of the anchoring elements. Before the ischemia tolerance of the tissue is reached, i.e., at the latest after a few hours, the tensile force must be lifted, or at least reduced far enough that blood flow to the tissue is once again possible on the pressure side of the anchoring element. In such a cyclical stretching, temporal regeneration intervals during which the skin is not stretched are placed between the intervals of stretching and thus stimulation of tissue proliferation.

Because the first and second anchoring elements may be adjusted independently of one another on the guide device, the tensile forces working on the skin via the first and second anchoring elements may also be varied independently of one another. For example, individual anchoring elements may be set to a high tensile force, which causes a strong degree of proliferation, said anchoring elements optionally exceeding the ischemic threshold on the pressure side of the anchoring elements. At the same time, the tensile force is reduced for the other anchoring elements in such a way that the skin tissue before these anchoring elements is again able to recover with good blood perfusion. In corresponding time cycles, the function of the anchoring elements is interchanged, such that the skin tissue that was previously under a high degree of tensile stress is able to recover, and the tensile force is exerted via the anchoring elements that were previously relaxed. Because some of the anchoring elements are always exerting a high degree of tensile force on the skin, the skin is constantly under a high degree of tensile force that is advantageous for tissue proliferation without causing damage to the tissue. The introduction of this high degree of tensile force into the skin changes its position in a cyclical manner.

In wound treatment, situations may also occur in which the skin should be stretched only in the region of one edge of the wound, while stretching of the skin on the opposite edge of the wound is not desired, for example, because the edge of a bone is located below this edge of the wound. In such a situation, the device according to the invention may be advantageously used in that, on the edge of the wound where no skin stretching is to occur, the first anchoring element and subsequent second anchoring elements are anchored in the skin and adjusted on the guide device such that the second anchoring elements do not exert any tensile force on the skin. Here, the second anchoring elements only serve to fix the device on the one side of the wound in a large-area of the skin without stretching the skin in order to support the tensile force acting on the other edge of the wound for the purpose of stretching the skin.

The guide device, the anchoring elements, and the adjustment of the anchoring elements on the guide device may be embodied in different ways. It is essential that the anchoring elements be adjustable on the guide device and be held in their respective adjusted position in order to be able to adjust and maintain the respective tensile force of the individual anchoring element in an individual fashion. The guide device may be made of rigid guides or a flexible band. The anchoring elements may be hooks that are insertable into the skin and be disposed individually or in rows in the anchoring elements. The anchoring elements may also be anchored in the skin in the form of safety needles. The tensile force exerted by the anchoring elements on the skin may be induced by the positional adjustment of the anchoring elements and thus by the stretching of the skin against its elasticity. In addition, spring forces may also reinforce and influence the tensile force.

The adjustment of the anchoring elements may occur manually in a simple fashion, for example, in accordance with a predetermined timetable or in accordance with a current evaluation of the skin and wound situation. It is also possible for the adjustment of the anchoring elements to be caused by motorized drive systems. Such drive systems may be controlled according to a predetermined or programmable plan in a temporal fashion or with regard to the respective tensile force. Finally, a regulated automatic adjustment of the anchoring elements is possible. To this end, it is preferably for the tensile force introduced into the skin by each of the anchoring elements to be measured, which is a function of the skin stretching currently occurring, and for the tensile force of the anchoring elements to be regulated to a target value that may be predetermined. Thus, an optimization of skin distraction is possible over longer periods of time without effort by personnel.

BRIEF DESCRIPTION OF THE DRAWINGS

The invention shall be described in greater detail in the following with reference to exemplary embodiments shown in the drawings, which show.

DETAILED DESCRIPTION OF THE ILLUSTRATED EMBODIMENTS

Figure 1:
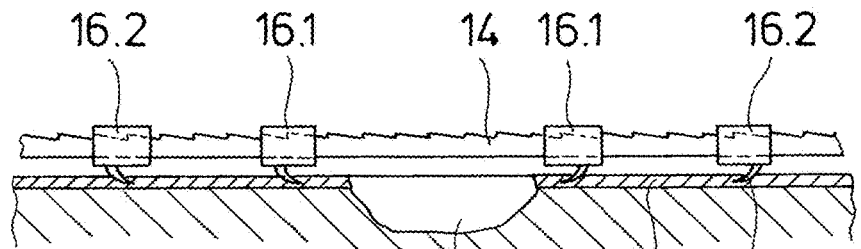
FIG. 1 a side view of a device for stretching the skin in a first embodiment.
Figure 2:
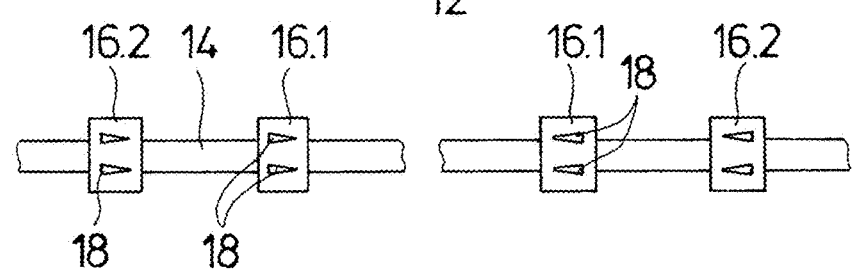
FIG. 2 a view of the device according to FIG. 1 from below.

In the first exemplary embodiment of FIGS. 1 and 2, a device is shown for stretching the skin. FIG. 1 shows one of the most important uses of this device, namely the stretching of the skin 10 at the edges of a wound 12 in order to pull the skin 10 of the edges of the wound together and to close the wound 12.

The device has a guide device that is embodied as a flexible band 14 in the exemplary embodiment shown in FIGS. 1 and 2 and is preferably made of plastic. Anchoring elements 16 are disposed on the band 14. The anchoring elements 16 may be fixed on the band 14 in the longitudinal direction of the band 14 in their respective adjusted positions. The anchoring elements 16 are designed such that they may be anchored in the skin 10.

In the exemplary embodiment shown, the anchoring elements 16 have hooks 18 on their underside that are inserted into the skin 10 in order to hook and anchor the anchoring elements 16 into the skin 10. Other designs of the anchoring elements are known as well and may be used as an alternative to the hooks 18. Preferably, the anchoring elements 16 may also have anchors in the form of safety needles as is shown, for example, in U.S. Pat. No. 4,896,680. In this embodiment, the anchoring elements 16 have a safety needle that is disposed transverse to the longitudinal extension of the band 14 and is inserted into the skin 10. The advantage of a design of the anchoring elements 16 with hooks 18 lies in the fact that the hooks 18 may simply be placed in the skin 10 and may be arranged with a greater freedom of variation in the transverse direction relative to the band 14. The advantage of anchoring elements 16 with a safety needle lies primarily in the fact that this anchor in the form of a safety needle cannot be unintentionally released from its anchoring in the skin 10.

As is shown in FIGS. 1 and 2, two first anchoring elements 16.1 sit on the band 14 and are inserted into the skin 10 opposite one another on the opposite edges of the wound 12. The first anchoring elements 16.1 may be slid relative to one another on the band 14 such that their distance from one another in the longitudinal direction of the band 14 is reduced and the intermediate area between the first anchoring elements 16.1, in the present case the region of the wound 12, is reduced. The skin 10 forming the edges of the wound 12 is thus stretched in the longitudinal direction of the band 14 such that the edges of the wound are moved toward one another in order to close the wound 12. If the skin at the edges of the wound is stretched far enough that the opposing edges of the wound are touching, the edges of the wound may be stitched or clamped to one another in order to close the wound 12.

The stretching of the skin 10 induces an increased tissue proliferation in the region in which the skin 10 is stretched such that the stretching of the skin 10 leads to an enlargement of the available skin area. The greater the tensile force exerted on the skin by the anchoring elements 16, the greater the tissue proliferation. In conventional devices that have only first anchoring elements 16.1 that are anchored in the skin 10 of the edges of the wound, the tensile force acting on the skin is limited. The anchoring elements 16, for example, the hooks 18, exert a pressure on their front side pointing in the pull direction on the tissue that corresponds to the tensile force applied. If this pressure exceeds the so-called ischemic threshold, this pressure hinders circulation through the tissue. This ischemic state can only exist for a limited amount of time because otherwise the tissue will become necrotic. In the known devices, the tensile force must therefore be kept below the ischemic threshold, which results in a lesser degree of skin stretching and tissue proliferation, or the tensile force must be interrupted at regular intervals for a recovery phase to allow circulation through the tissue, which also reduces the effectiveness of the skin stretching. Finally, the range of the tensile forces introduced into the skin is limited to a few centimeters. The tensile force introduced into the skin 10 via the anchoring elements 16 reduces exponentially with the distance from the anchoring element 16 and, in human skin, for example, has fallen to zero after approximately 5 or 6 centimeters. This means that only a correspondingly limited area of skin is mobilized by the applied tensile forces and stimulated to produce tissue proliferation.

In order to eliminate or reduce these problems, at least one second anchoring element 16.2 is provided according to the invention in addition to the pair of first anchoring elements 16.1. In the exemplary embodiment shown in FIGS. 1 and 2, one second anchoring element 16.2 is associated with each of the first anchoring elements 16.1. The second anchoring elements 16.2 are preferably designed in the same fashion as the first anchoring elements 16.1. The second anchoring elements 16.2 may therefore also be slid on the band 14 and locked in their respective adjusted positions.

In FIG. 1, for example, a first anchoring element 16.1 has been inserted into the skin 10 of the right-hand side of the wound 12. A second anchoring element 16.2 is disposed on the band 14 on the side of the first anchoring element 16.1 facing away from the wound 12. This second anchoring element 16.2 is anchored in the skin 10 at a distance from the first anchoring element 16.1 in the longitudinal direction of the band 14. Corresponding to the range of the tensile forces in skin 10, this distance may be 1 to 20 cm depending on the application, for human skin, the distance is generally 1.5 to 3 cm. The second anchoring element 16.2 exerts a tensile force on the skin 10 that is generated by the adjustment of the second anchoring element 16.2 on the band 14 against the wound 12, i.e., to the left in FIG. 1. In this manner, an additional area of skin to the right of the second anchoring element 16 determined by the range of the tensile force is mobilized and stimulated to generate tissue proliferation. In addition, the second anchoring element 16.2 causes a preliminary tensing of the skin 10 for the first anchoring element 16.1 disposed on the edge of the wound. Thus, a tensile force that can be determined by adjusting the first anchoring element 16.1 relative to the second anchoring element 16.2 acts on the skin region between the first anchoring element 16.1 and the second anchoring element 16.2.

A corresponding arrangement of a first anchoring element 16.1 and a second anchoring element 16.2 is shown in FIG. 1 on the left-hand side of the wound 12. It is easily discernible that the second anchoring element 16.2 may also be provided on only one side of the wound 12, such that only one single first anchoring element 16.1 is provided on one side of the wound. In addition, it is easily discernible that more than one second anchoring element 16.2 may also be disposed on one side behind the first anchoring element 16.1. If two or more second anchoring elements 16.2 are disposed one behind the other, then these second anchoring elements are adjustable and lockable independently of one another in the longitudinal direction of the band 14 and their functions add up in the manner described above.

The device as shown in FIGS. 1 and 2 offers the following use options and advantages:

By virtue of the anchoring elements 16.1 and 16.2 disposed one behind the other, it is possible to stretch larger areas of the skin in the direction of the longitudinal extension of the band 14, i.e., in the stretching direction, and to activate tissue proliferation in those areas. Because a larger tissue area is being mobilized, a larger skin yield results for closing the wound 12 with the same tissue proliferation per area.

The second anchoring elements 16.2 generate a preliminary tension of the skin for the additional second anchoring elements 16.2 or the first anchoring element 16.1 following in the pull direction. The tensile force introduced into the skin at points by the individual anchoring elements 16.1, 16.2 may therefore be selected at a lower level. Even with a lower tensile force of the individual anchoring elements, a stretching of the skin and skin yield may be obtained that is attainable using conventional means only at a substantially higher level of tensile force. Even if the force introduced by the individual anchoring elements lies below the ischemic threshold, an effective skin yield may be obtained.

In an additional use of the device according to the invention, the tensile forces introduced into the skin 10 via the first anchoring element 16.1 and via the one or more second anchoring elements 16.2 may be varied over time. For example, in a first time period, a high degree of tensile force is introduced into the skin 10 via the first anchoring element 16.1 that exceeds the ischemic threshold on the pressure side of the anchoring element 16.1. At the same time, the second anchoring element 16.2 is exerting only a low level of tensile force on the skin 10 or is completely relaxed. In a subsequent time period, the first and second anchoring elements exchange roles. The second anchoring element 16.2 is set such that it introduces a very high level of tensile force into the skin 10, which may exceed the ischemic threshold on the pressure side of the second anchoring element 16.2. During this time period, the tensile force introduced by the first anchoring element 16.1 is reduced or completely eliminated. These periods then repeat themselves cyclically. In this manner, a high level of tensile force is being introduced into the skin 10 via one of the anchoring elements 16.1 or 16.2, which leads to a high degree of tissue proliferation. The other anchoring element 16.1 or 16.2 is relaxed or relaxed to the extent that the tissue on the pressure side of the anchoring element again has good and complete blood circulation and is able to regenerate. Overall, therefore, the skin 10 may be stretched with a very high degree of tensile force in an uninterrupted fashion for the entire duration of treatment, with the contact points of these tensile forces changing in a cyclical manner, such that the tissue is constantly able to regenerate sufficiently. Because the high degree of tensile force is constantly acting on the skin 10 at different contact points, a very effective stretching and tissue proliferation is attained.

FIG. 2 shows an embodiment in which each anchoring element 16.1, 16.2 has two hooks 18 next to one another transverse to the longitudinal direction of the band 14. Such an embodiment allows the introduction of force into a relatively narrow section of the edge of the wound. In the case of a larger wound 12, the edge of the wound may be stretched in an individual fashion by a plurality of devices disposed one next to the other.

Figure 3:
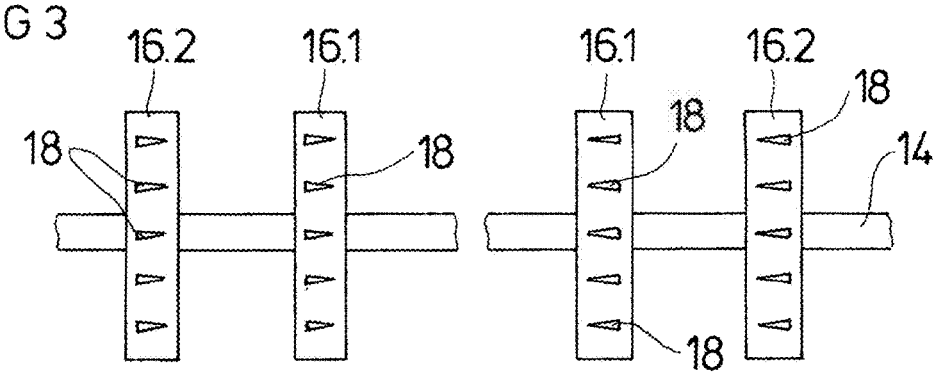
FIG. 3 a view from below of a modification of this device.

FIG. 3 shows a modification in which the anchoring elements 16.1, 16.2 have larger dimensions transverse to the longitudinal direction of the band 14 and thus may also have a plurality of hooks 18. This embodiment is suitable for stretching a wider breadth of the edge of the wound.

Figure 4:
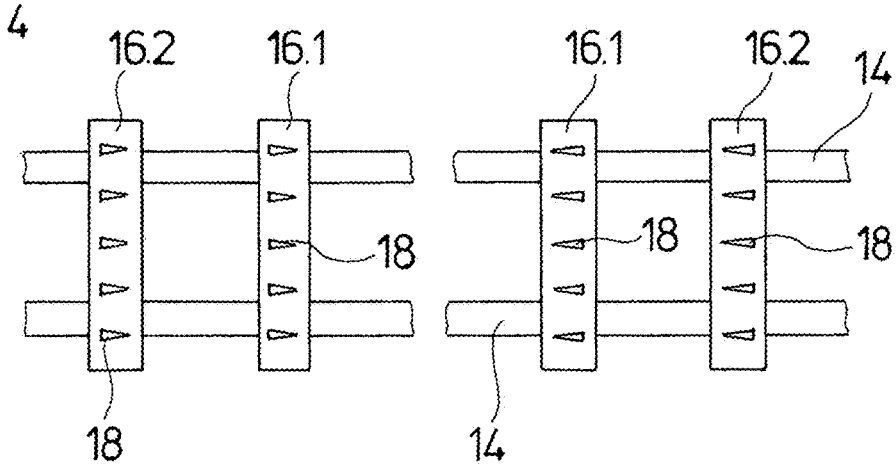
FIG. 4 a view from below of an additional modification of this device.

FIG. 4 shows an additional modification in which two bands 14 are provided running parallel to one another in the stretching direction, on which the respective anchoring elements 16.1, 16.2 are disposed in an adjustable and fixable manner. This embodiment provides a greater degree of stability with broad anchoring elements 16.1, 16.2. In addition, the anchoring element 16.1, 16.2 may be adjusted differently with both of its ends on the two bands 14. In this manner, the anchoring elements 16.1, 16.2 may also be set diagonally against the direction of the bands 14 and thus against the stretching direction, such that they may be adapted to the path of the edge of the wound.

Figure 5:
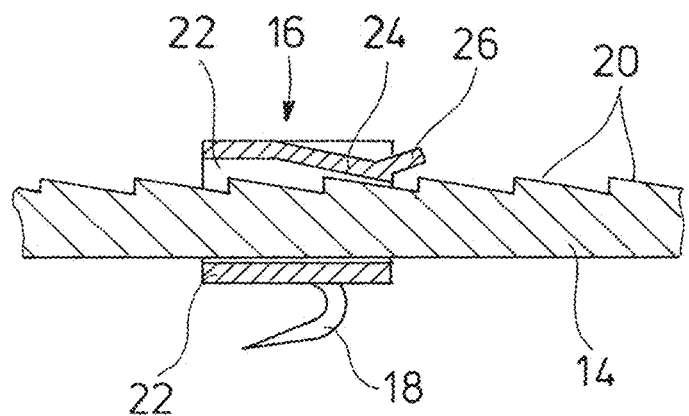
FIG. 5 a detail of the device of the first embodiment in a vertical section.
Figure 6:
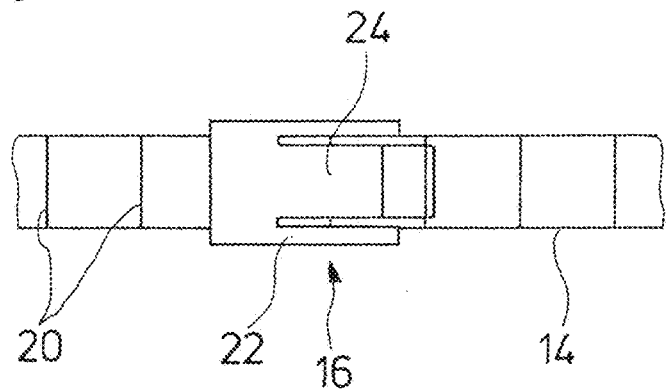
FIG. 6 a view of the detail from FIG. 5 from the top.

FIGS. 5 and 6 show an exemplary embodiment of an anchoring element 16 and its adjustability and fixability on the band 14. The flexible band 14 has transverse ribs 20 on its top side that may, for example, form a saw profile. The anchoring element 16 has, for example, a housing 22 made of plastic in the form of a box that surrounds the band 14. Hooks 18 are injected on the underside of the housing 22. The housing 22 is guided on the band 14 with its underside and side walls. The upper side of the housing 22 is designed with a locking tongue 24 that is preloaded against the top of the band 14. The locking tongue 24 rests against the top of the band 14 with a locking nose. As may be seen from FIG. 5, the design of the transverse ribs 20 in the form of a toothed saw and of the locking tongue 24 allows an adjustment of the anchoring element on the band 14 to the left. Here, the locking tongue 24 glides over the transverse ribs 20. However, in FIG. 5, the anchoring element 16 is locked against a movement of the anchoring element 16 to the right on the band 14 in that the locking tongue 24 is looked into the teeth of the transverse ribs 20 with its locking nose. A handling tip 26 on the free end of the locking tongue 24 allows the locking tongue to be lifted out of the locking of the transverse ribs 20 against its elastic force, such that the anchoring element 16 may be released from its locked position and moved to the right on the band 14 in FIG. 5.

Figure 7:
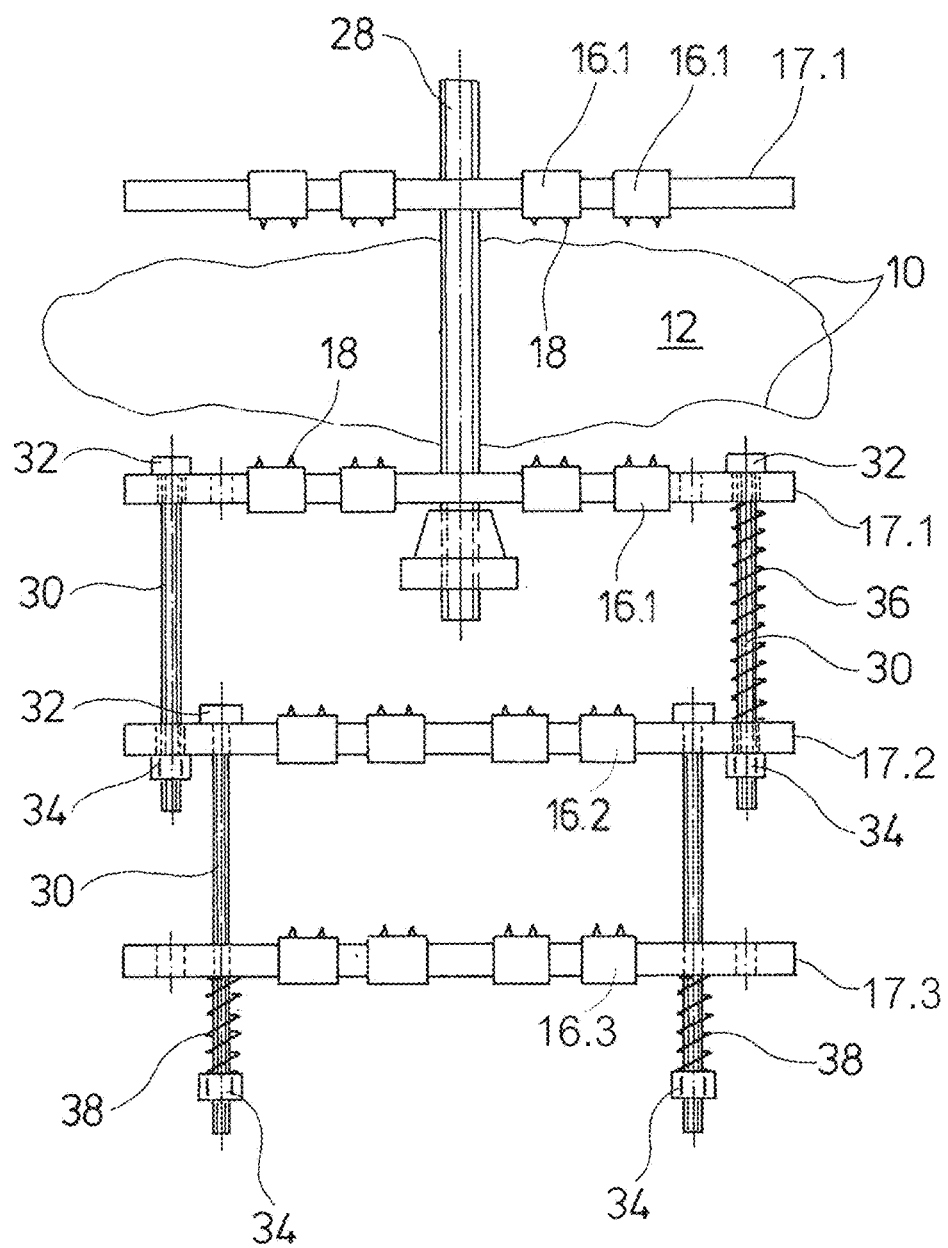
FIG. 7 a view of a second embodiment of the device from the top.

FIG. 7 shows another embodiment of the device. Insofar as this embodiment corresponds to the embodiment described above, the same reference characters have been used and reference is made to the above description.

In the exemplary embodiment according to FIG. 7, the guide device has a threaded spindle 28 on which the first anchoring elements 16.1 are adjustable opposite one another. The guidance of the first anchoring elements 16.1, the design of the threaded spindle 28, and the adjustability may be designed, for example, in the manner known from DE 44 44 130 A1. Other embodiments lie within the scope of the actions of the skilled practitioner.

As is shown in FIG. 7 for only one side of the device, a second anchoring element 16.2 may be connected to the first anchoring element 16.1. The threaded rods 30 disposed on the outer ends of the anchoring elements 16.1 and 16.2 serve to connect and to guide the second anchoring element 16.2 on the first anchoring element 16.1. The threaded rods 30 penetrate continuous bores in the anchoring elements 16.1 and 16.2. The threaded rods 30 are held on the anchoring element 16.1 by a head 32. A threaded nut 34 is screwed onto the opposite end that is guided through the second anchoring element 16.2. By adjusting the threaded nut 34 on the threaded rod 30, the distance between the first anchoring element 16.1 and the second anchoring element 16.2 may be set and fixed. In the stretching direction, i.e., in the direction of the threaded rods 30, the anchoring elements 16.1 and 16.2 are held at their distance limited by the threaded nut 34 by the elastic tensile stress of the skin. Optionally, the anchoring elements 16.1 and 16.2 may still be kept adjacent to the head 32 and the threaded nut 34 by an additional screw pressure spring 36 sitting on the threaded rod 30. By adjusting the threaded nuts 34 on the threaded rods 30, the second anchoring element 16.2 may be pulled relative to the first anchoring element 16.1 in order to adjust the tensile force introduced into the skin 10 by the second anchoring element 16.2. In so doing, the first anchoring element 16.1 is supported via the threaded spindle 28 and the anchoring elements on the other side of the wound 12.

In a corresponding manner, additional second anchoring elements 16.2 may be connected to the second anchoring element 16.2, as is shown in FIG. 7 for an additional anchoring element 16.2. The connection and the adjustability between the consecutive second anchoring elements 16.2 corresponds to the connection and adjustability between the first anchoring element 16.1 and the second anchoring element 16.2.

An additional variant is shown for connecting and guiding the two consecutive second anchoring elements 16.2. A screw pressure spring 38 is placed between the threaded nut 34 and the anchoring element 16.2. The screw pressure spring 38 presses the corresponding anchoring element 16.2 in the pull direction of the device. The screw pressure spring 38 thus determines the tensile force exerted on the skin 10 by the anchoring element 16.2. The screw pressure spring 38 may be provided with initial tension by means of the threaded nut 34 for the purpose of setting this introduced tensile force. The screw pressure spring 38 maintains this force introduced into the skin 10 via the anchoring element 16.2 even over a certain movement path of the anchoring element 16.2. Even when the skin 10 stretches under the effect of the introduced tensile force and the anchoring element 16.2 wanders on the threaded rods 30, the introduced tensile force is maintained by the screw pressure spring 38. Readjustment of the threaded nuts 34 in order to adjust the active tensile force therefore only becomes necessary over longer time intervals.

The embodiment according to FIG. 7 clearly shows how, by the respective adjustment of the first anchoring elements 16.1 on the threaded spindle 28 and the mutual adjustment of the anchoring elements 16.1 and 16.2 via the threaded rods 30 and the threaded nuts 34, switching between a pulling phase and regeneration phase is also possible by mutual adjustment.

If the device is designed in an essentially symmetrical fashion on both sides of the wound 12, as is shown by embodiment described above, an adjustable tensile force is essentially exerted on the skin 10 on both edges of the wound. The skin 10 is correspondingly stretched on both edges of the wound.

However, there are cases in which the skin is to be stretched on only one side of the wound 12 to the greatest extent possible while stretching of the skin is not desired on the other edge of the wound, for example, because pressure-exerting structures are located below this region of skin.

Figure 8:
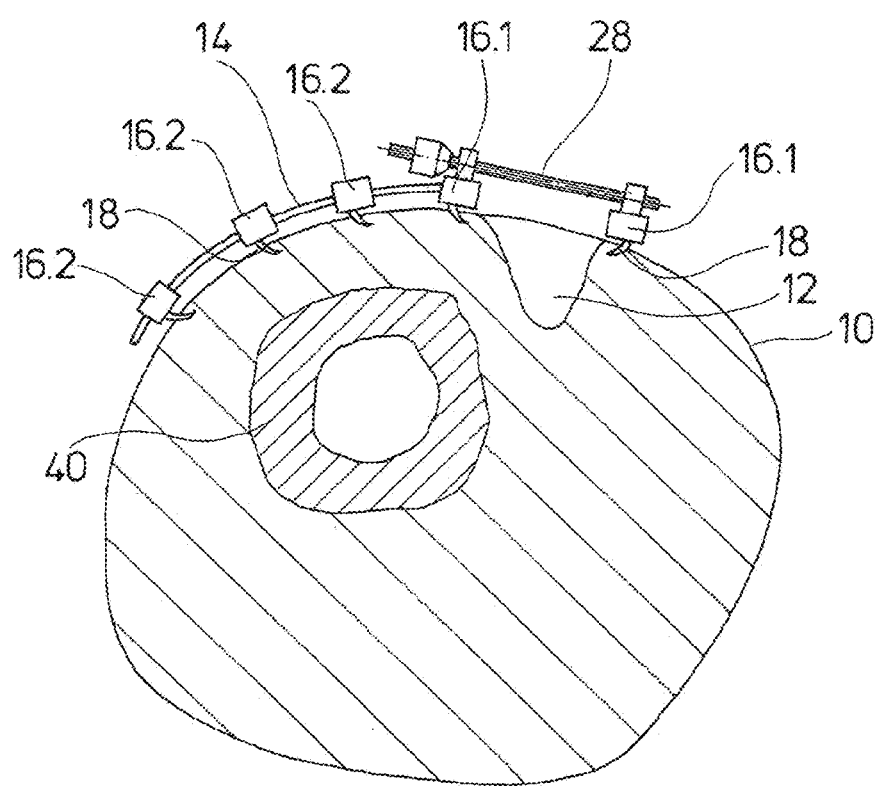
FIG. 8 an exemplary use of the device.

FIG. 8 shows such a case in which a wound 12 is located adjacent to the edge of a bone 40.

In this case, the device is anchored with a first anchoring element 16.1 (and, optionally, with additional second anchoring elements 16.2 as well) in the edge of a wound whose skin is to be stretched. On the side of the wound where the skin 10 is not to be stretched, a first anchoring element 16.1 and one or, preferably, more second anchoring elements 16.2 are anchored in the skin 10. The distances between the first anchoring element 16.1 and the subsequent anchoring elements 16.2 is not adjusted in this case, such that the skin 10 between the first anchoring element 16.1 and the consecutive second anchoring elements 16.2 is not subjected to any tensile force and is not stretched. The anchoring elements 16.2 thus achieve an anchoring for the first anchoring element 16.1 that is as tension-free as possible over a large area. If the anchoring elements 16.1, which are respectively anchored on the opposite edges of the wound 12, are pulled toward one another by means of the threaded spindle 28, this leads to an asymmetrical stretching of the skin 10 on the edge of the wound 12 that is on the right-hand side in FIG. 8. In contrast, the opposing force for supporting the tensile force exerted by the anchoring element 16.1 on the right-hand edge of the wound is distributed over a large area of the skin by the first anchoring element 16.1 and the subsequent anchoring elements 16.2 on the left-hand side of the wound in FIG. 8, such that virtually no tensile force is introduced into the skin there by the individual anchoring elements 16.1, 16.2.

LIST OF REFERENCE CHARACTERS

10 Skin
12 Wound
14 Band
16 Anchoring elements
16.1 First anchoring element
16.2 Second anchoring element
18 Hook
20 Transverse ribs
22 Housing
24 Locking tongue
26 Handling tip
28 Threaded spindle
30 Threaded rods
32 Head
34 Threaded nut
36 Screw pressure spring
38 Screw pressure spring
40 Bone

The invention claimed is:

1. A method for stretching skin to close a wound, comprising:
anchoring first anchoring elements, which are adjustably coupled to a guide device, to the skin on both sides of the wound, wherein a distance between the first anchoring elements is adjustable to introduce a first pulling tensile force in the skin in a pulling direction;
anchoring a second anchoring element in the skin on at least one side of the wound,
wherein the second anchoring element is anchored in the skin behind a first anchoring element of the first anchoring elements and at a distance from the first anchoring element in the pulling direction,
wherein the second anchoring element introduces a second pulling tensile force in the skin in the pulling direction; and
wherein the first pulling tensile force of the first anchoring elements and the second pulling tensile force are adjustable independently from each other.

2. The method according to claim 1, wherein the first tensile force and second tensile force are introduced at a distance of up to 20 cm.

3. The method according to claim 1, wherein the first tensile force and second tensile force introduced at a distance from one another in a direction are each less than the tensile force that would cause ischemia on a pressure side of the anchoring elements.

4. The method according to claim 1, further comprising:
anchoring a plurality of pairs of first anchoring devices such that each individual pair of first anchoring devices introduce the first pulling tensile force in the skin in the pulling direction;
wherein the each individual pair of first anchoring devices provides a different first pulling tensile force.

5. The method according to claim 4, further comprising cyclically switching comparatively high and low first pulling tensile forces between the plurality of pairs of first anchoring devices.

6. The method according to claim 5, wherein the high first pulling tensile force exceeds a value at which ischemia occurs on a pressure side of the anchoring element, and the low first pulling tensile force allows the circulation of blood in the tissue on a pressure side of the anchoring element.

7. The method according to claim 1, further comprising anchoring on one side of the wound a plurality of second anchoring elements disposed one behind the other in the pulling direction.

8. The method according to claim 1, further comprising introducing a tensile force into the skin in an asymmetrical fashion via the first anchoring element on a side of the wound without the second anchoring elements.

9. The method according to one of claim 1, further comprising manually adjusting the tensile forces introduced into the skin.

10. The method according to one of claim 1, further comprising adjusting of the tensile forces introduced into the skin.

11. The method according to claim 1, wherein the first tensile pulling force and the second tensile pulling force are parallel to each other.

12. The method according to claim 11, wherein the first tensile pulling force and the second tensile pulling force are parallel to the pulling direction.

13. A method for stretching skin to close a wound, comprising:
- anchoring opposing first anchoring elements in the skin on opposing sides of the wound, wherein the opposing first anchoring elements are adjustably attached to a guide device and the opposing first anchoring elements without penetrating beneath the skin;
- introducing a first pulling tensile force in the skin in a pulling direction by reducing a distance between the first anchoring elements along the guide device;
- anchoring a second anchoring element in the skin behind a first anchoring element of the opposing first anchoring elements;
- introducing a second pulling tensile force in the skin in the pulling direction via the second anchoring element;
- wherein the first pulling tensile force and the second pulling tensile force are adjustable independently from each other.

14. The method according to claim 13, further comprising:
- anchoring a plurality of pairs of opposing first anchoring devices such that each individual pair of opposing first anchoring devices introduce the first pulling tensile force in the pulling direction, wherein the first pulling tensile force provided by each individual pair of opposing first anchoring devices is different;
- cyclically switching comparatively high and low first pulling tensile forces between the plurality of pairs of opposing first anchoring devices.

15. The method according to claim 13, further comprising:
- anchoring on one side of the wound a plurality of second anchoring elements disposed one behind the other in the pulling direction.

16. The method according to one of claim 13, further comprising:
- obtaining distance measurements indicating a distance the skin is stretched;
- adjusting the first tensile force based on the distance measurements.

17. The method according to claim 13, wherein the first tensile pulling force and the second tensile pulling force are parallel to each other and parallel to the pulling direction.

18. The method according to claim 17, wherein the first tensile pulling force and the second tensile pulling force are parallel to the pulling direction.

* * * * *